United States Patent
Whitley

(10) Patent No.: US 7,163,115 B2
(45) Date of Patent: Jan. 16, 2007

(54) ROLLER BOTTLE CAP

(75) Inventor: Kenneth W. Whitley, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/667,007

(22) Filed: Sep. 19, 2003

(65) Prior Publication Data

US 2004/0099629 A1    May 27, 2004

Related U.S. Application Data

(60) Provisional application No. 60/412,356, filed on Sep. 20, 2002.

(51) Int. Cl.
*B65D 45/00* (2006.01)

(52) U.S. Cl. .................................. 215/276; 215/350

(58) Field of Classification Search ............... 215/276, 215/354, 350, 345, 343, 349, 351, 363, 320, 215/279, 277
See application file for complete search history.

(56) References Cited

U.S. PATENT DOCUMENTS

| | | | | |
|---|---|---|---|---|
| 1,985,703 A * | 12/1934 | Wheaton | .................. | 401/119 |
| 3,499,568 A * | 3/1970 | Riera | ....................... | 215/276 |
| 3,709,395 A * | 1/1973 | Brennan et al. | ............ | 215/247 |
| 3,924,772 A * | 12/1975 | Magnani | .................... | 215/276 |
| 4,128,184 A * | 12/1978 | Northup | .................... | 215/222 |
| 4,423,821 A * | 1/1984 | McIntosh | .................. | 215/329 |
| 4,462,502 A * | 7/1984 | Luenser et al. | ............. | 215/329 |
| 4,747,500 A * | 5/1988 | Gach et al. | ................ | 215/250 |
| 4,880,127 A * | 11/1989 | Doi | ........................... | 215/252 |
| 5,092,477 A * | 3/1992 | Johnson et al. | ............. | 215/230 |
| 5,358,872 A | 10/1994 | Mussi et al. | | |
| 5,391,496 A | 2/1995 | Kayal et al. | | |
| 5,421,469 A * | 6/1995 | Lee | ........................... | 215/274 |
| 5,578,491 A | 11/1996 | Kayal et al. | | |
| 5,586,673 A * | 12/1996 | Venooker et al. | .......... | 215/310 |
| 5,595,907 A | 1/1997 | Kayal et al. | | |
| 5,622,865 A | 4/1997 | Kayal et al. | | |
| 5,695,987 A | 12/1997 | Kayal et al. | | |
| 5,766,936 A | 6/1998 | Kayal et al. | | |
| 5,984,124 A * | 11/1999 | Takano | ....................... | 215/252 |
| 6,502,710 B1 * | 1/2003 | Bosl et al. | .................. | 215/351 |
| 2003/0127421 A1* | 7/2003 | Ziegler et al. | | |
| 2004/0108294 A1* | 6/2004 | Bloom et al. | | |

FOREIGN PATENT DOCUMENTS

| | | |
|---|---|---|
| EP | 0 614 967 | 9/1994 |
| EP | 1 066 881 | 1/2001 |
| WO | WO 91/01238 | 5/1981 |
| WO | WO 02/072265 | 9/2002 |

* cited by examiner

*Primary Examiner*—Lien M. Ngo

(57) ABSTRACT

A two-piece cap assembly for closing an opening in a neck portion of the container is provided that includes a cap body having a top wall and a depending annular skirt for screw attachment to the neck portion of the container. A plug seal is attachable to the underside of the top wall of the cap body. The plug seal and the cap body are relatively rotatably coupled for independent rotation of the cap body with respect to the plug seal upon attachment and detachment of the cap to the neck portion of the container.

19 Claims, 4 Drawing Sheets

ROLLER BOTTLE CAP

This application claims the benefit of U.S. Provisional Application No. 60/412,356, filed Sep. 20, 2002.

BACKGROUND OF THE INVENTION

1. Field of the Invention

This invention relates to a cap for closure of the liquid opening of a container, and more particularly to a two-piece cap for a roller bottle.

2. Description of Related Art

One type of container commonly used in the laboratory for culturing of cells is known as a "roller bottle". Roller bottles are generally cylindrically shaped and are adapted to rotate about their axes. The internal surfaces of such roller bottles are for providing active surfaces for cells. Following introduction of a liquid growth medium into the liquid opening of the roller bottle, the bottle is capped. The subsequent rotating movement of the bottle keeps the internal surfaces wetted with a liquid medium, thereby encouraging the growth of cells. Rotating rollers of an appropriate apparatus are employed to rotate these roller bottles.

Current caps used to seal the liquid opening of roller bottles, as well as flasks and centrifugal tubes are screw-on caps of a one-piece design. The mechanical advantage of a screw-type threaded cap is translated to an axial force, wedging the sealing mechanism into the inner rim of the container, forming a tight seal due to the interference fit between the sealing mechanism and the container rim. With the current caps, some of the torque required to seal and unseal the bottle is generated by the friction created when the sealing mechanism rubs against the container rim as it rotates with the cap during assembly and disassembly. The elimination or reduction of this friction translates to a lower torque required to attach and detach the cap from the container.

A problem associated with the one-piece design of the cap has been the large amount of torque required to remove the cap from bottles once the seal-area has become crusted with dried media. In particular, the roller bottle user must apply an especially high amount of torque to remove caps that are stuck to the bottle because the media contained within the bottle has dried between the cap and the bottle rim, acting as an adhesive. To remove a one-piece cap, the user must rotate the cap and grind the dried media against the sealing surface as the sealing surface rotates against the inner bottle rim.

A need exists, therefore, for an improved cap for roller bottles, flasks, centrifugal tubes and other containers where the ability of the user to attach and detach the cap using a low amount of torque is of importance. In particular, it would be advantageous to provide a cap with a sealing mechanism that was free to rotate about the axis of the cap, so that rather than rubbing against the inner rim of the bottle as the cap rotates, the sealing mechanism instead moves up or down as the cap moves up or down.

SUMMARY OF THE INVENTION

The present invention provides a cap assembly for closing an opening in a neck portion of a container. The cap assembly includes a cap body having a top wall and a depending annular skirt for screw attachment to the neck portion of the container. A plug seal is attachable to an underside of the top wall of the cap. The plug seal and the cap are relatively rotatably coupled for independent rotation of the cap body with respect to the plug seal upon attachment and removal of the cap assembly from the neck portion of the container.

DETAILED DESCRIPTION OF THE INVENTION

Figure 1A:
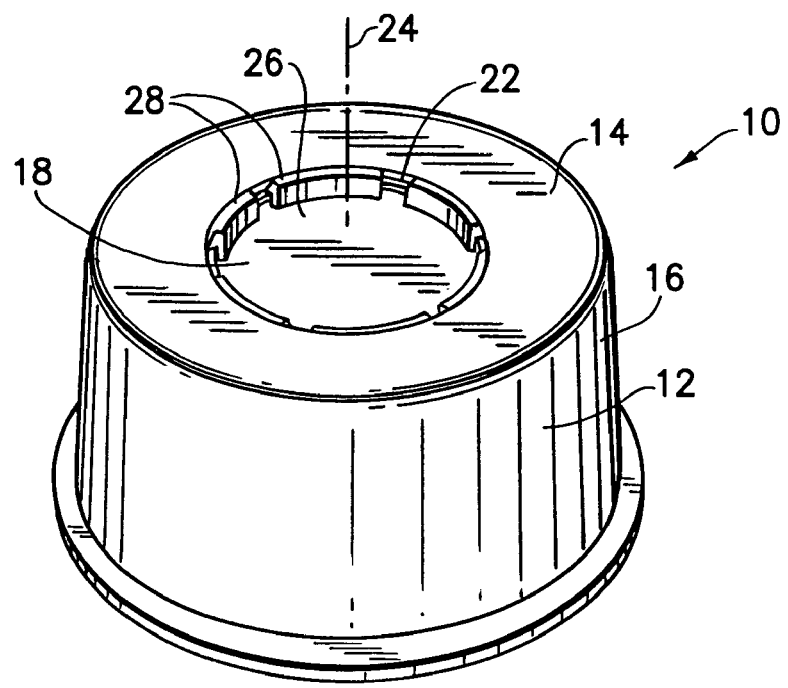
FIG. 1A is top perspective view of the two-piece cap assembly of the present invention.
Figure 1B:
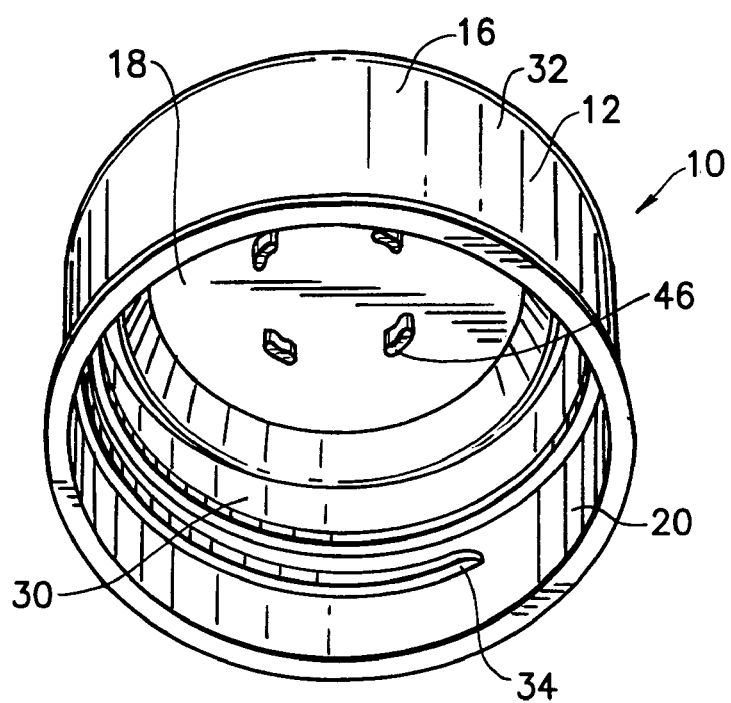
FIG. 1B is a bottom perspective view of the cap assembly of FIG. 1A.

Referring now to the drawings, in which like reference characters refer to like parts throughout, FIGS. 1A and 1B show a cap assembly for closing the liquid opening in a neck portion of a container in accordance with the present invention. In particular, FIGS. 1A and 1B show a roller bottle cap assembly 10. As can be seen, cap assembly 10 includes a cap body 12 having a top wall 14 and a depending annular skirt 16 for screw attachment to the neck portion of a roller bottle, and further includes plug seal 18 which is attachable to the underside 20 of cap body 12. Plug seal 18 and cap body 12 are relatively rotatably coupled for independent rotation of the cap body 12 with respect to plug seal 18 upon attachment and removal of the cap assembly 10 from the neck portion of the roller bottle or other container.

In contrast to prior art one-piece caps, with the two-piece cap assembly of the present invention, some of the torque required to attach and detach the cap body from the neck of a container is eliminated because the sealing mechanism does not have to rotate as the cap is rotated during attachment and detachment of the cap body. In particular, plug seal 18 is free to rotate about cap body axis 24, so that rather than rubbing against the inner rim of the bottle as the cap body rotates, it simply moves up or down as the cap body moves up or down.

Figure 2A:
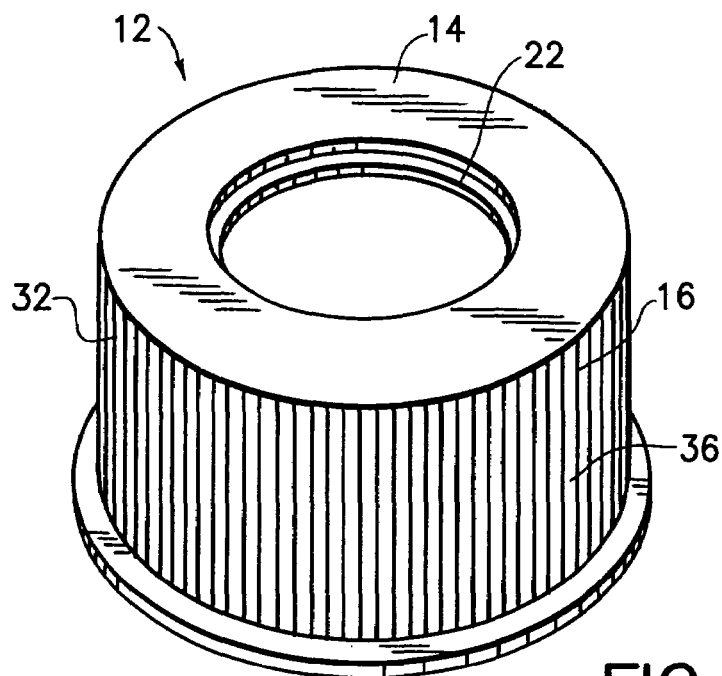
FIG. 2A is a top perspective view of the cap body of the inventive cap assembly.

With reference now to FIGS. 1A and 2A, in one embodiment, the cap body 12 of the inventive cap assembly includes a central orifice 22 for accommodating plug seal component 18. The orifice 22 may be stepped to help provide a snap-fit with plug seal 18.

Figure 2B:
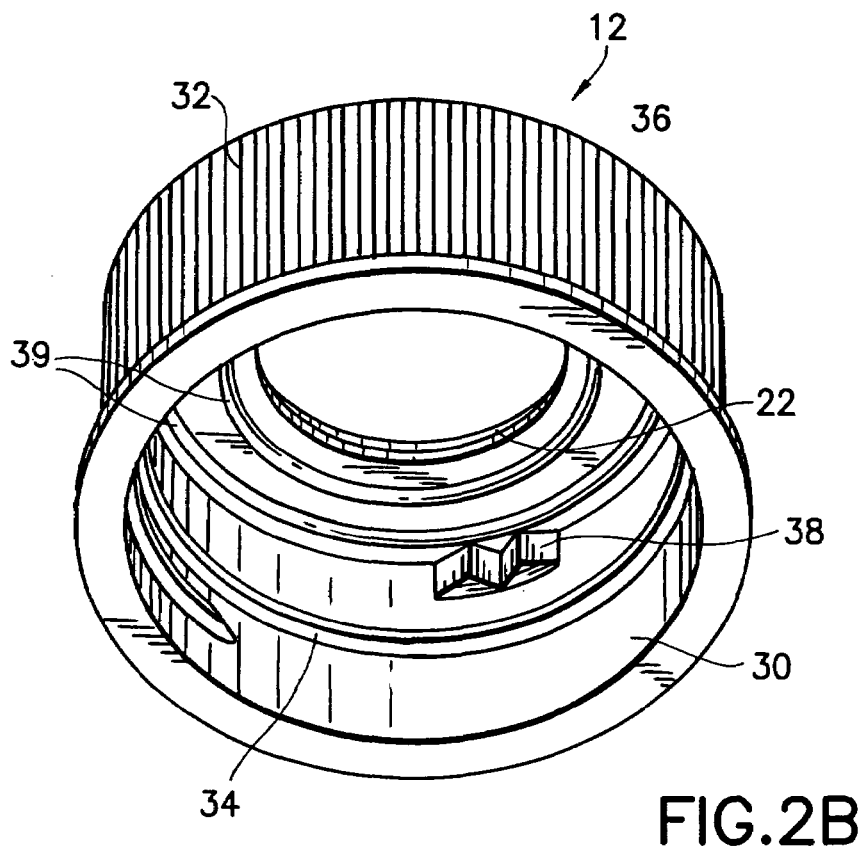
FIG. 2B is bottom perspective view of the cap body of FIG. 2A.

As shown in FIGS. 1A and B and FIGS. 2A and B annular skirt 16 of cap body 12 includes an inner wall 30 and an outer wall 32. The inner wall 30 may include threads 34 for removably attaching the cap assembly 10 from the neck portion of the container. As shown in FIGS. 2A and 2B, outer wall 32 of annual skirt 16 may include vertical ribs 36 to improve the user's grip during attachment and detachment of the cap. Inner wall 30 may include a locking arrangement 38, as shown in FIG. 2B, for holding the cap assembly in a locked open position on the roller bottle for maintaining the roller bottle open to the environment surrounding it. With further reference to FIG. 2B, the underside of top wall 14 of cap body 12 preferably includes two projecting rings 39 which reduce surface contact between cap body 12 and plug seal 18. Desirably, such rings are integrally formed with the cap.

Figure 3A:
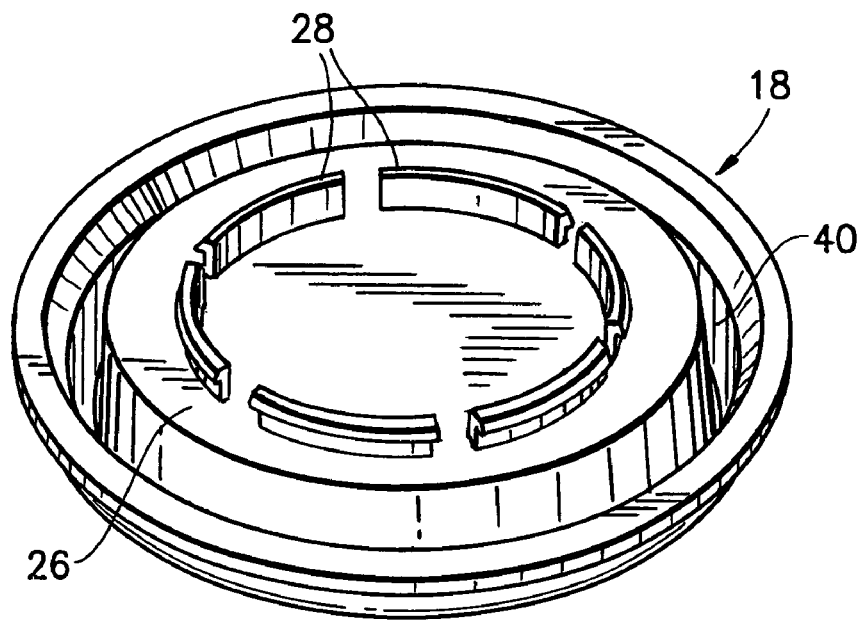
FIG. 3A is a top perspective view of the plug seal component of the inventive cap assembly.

Referring now to FIGS. 1A and 3A, top surface 26 of plug seal 18 includes flanges 28 to provide a snap-fit attachment to the underside of the cap body. Flanges 28 may be integrally formed with top surface 26 of plug seal 18 and are configured in an annular ring for association with orifice 22. As needed, the orifice may be stepped to help provide the snap-fit, as described above.

Figure 4:
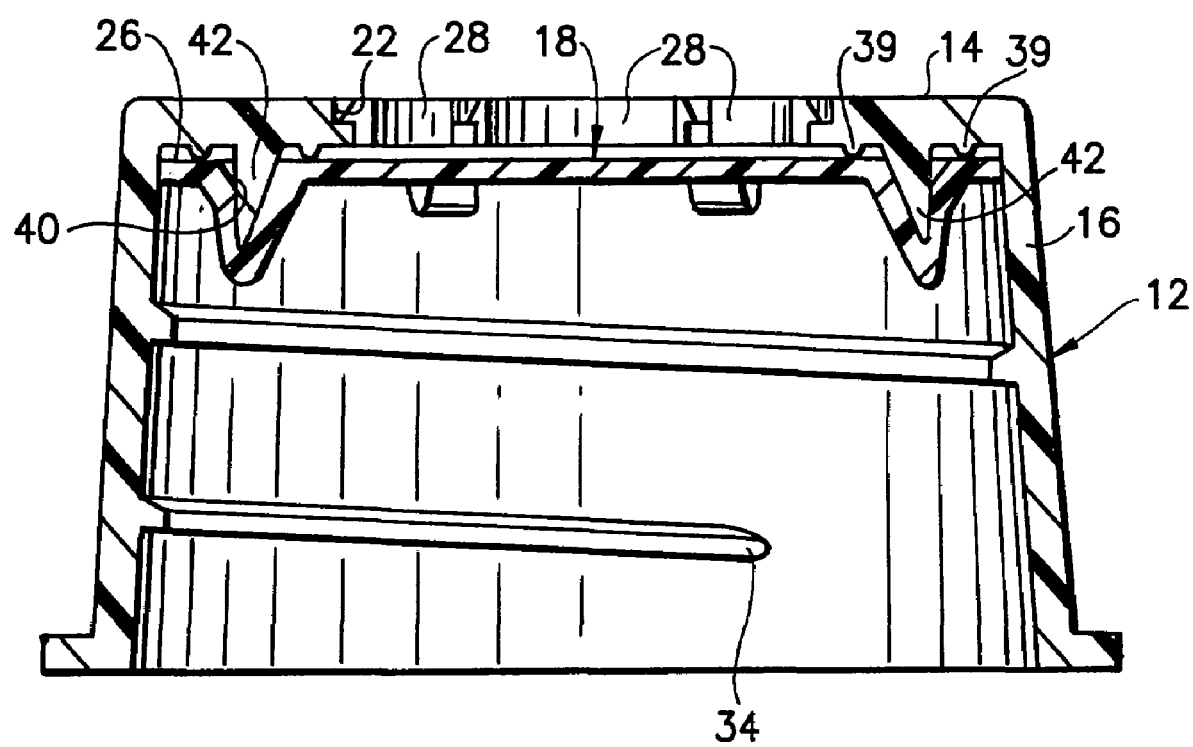
FIG. 4 is a cross-sectional showing of the cap assembly of the present invention.

As shown in FIGS. 3A and 4, top surface 26 of plug seal component 18 cap assembly 10 includes an annular groove 40 to help further provide a snap-fit attachment with cap body 12. In particular, as shown in the cross-sectional view of FIG. 4, top wall 14 of cap body 12 may include depending annular projections 42 spaced radially from depending annual skirt 16 to help provide a snap-fit with the annular groove 40 of plug seal 18.

Figure 3B:
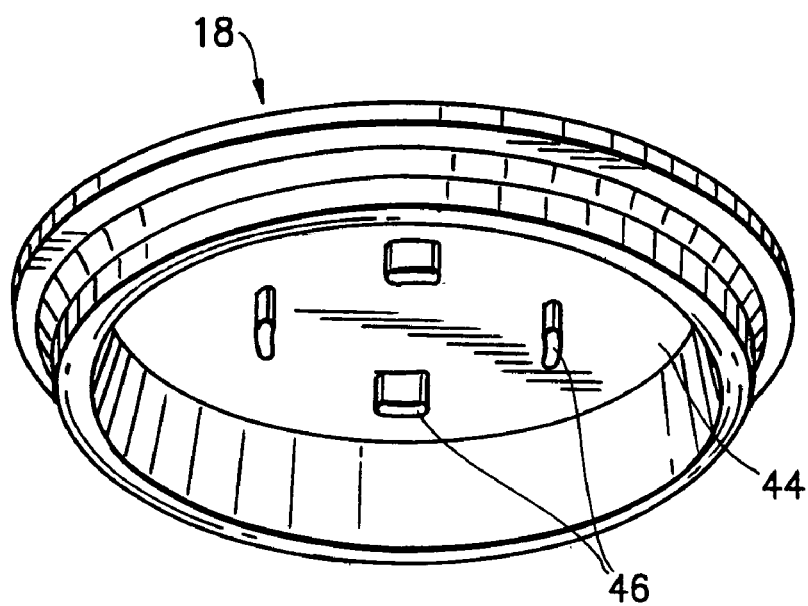
FIG. 3B is a bottom perspective view of the plug seal of FIG. 3A.

Referring now to FIG. 3B, in one embodiment, bottom surface 44 of plug seal component 18 includes tabs 46 in a spaced annular arrangement for insertion of a device (not shown) to form a vented cap assembly. For example, the tabs 46 may permit attachment of a gas-permeable membrane to permit free passage of oxygen and carbon dioxide while preventing passage of bacteria and fungi into the roller bottle. Suitable gas-permeable membranes can be made of materials such as polyethylene, polycarbonate, acrylic co-polymers and polytetrafluoroethylene.

In viewing conditions for producing cap assemblies in accordance with the invention, a variety of thermoplastic materials may be utilized, including, for example, polystyrene, polyethylene terephthalate, the polyolefins and polyvinylchloride.

In contrast to prior art caps, the sealing mechanism of the present invention rotates independently about the axis of the cap. The sealing mechanism does not rotate as the cap rotates, thereby eliminating the friction normally occurring when the sealing mechanism rubs against the container rim as it rotates with the cap. Therefore, lower torque is required to attach and detach the cap from the container. This represents a significant advantage in situations where media contained within the roller bottle dries against the cap and bottle rim, acting as an adhesive. With prior art one-piece roller bottle caps, the user was required to rotate the cap and grind the dried media against the sealing surface as the sealing surface rotated against the inner bottle rim. However, with the two-piece design, the sealing surface is lifted free of the crusted media at the bottle rim, rather than grinding against it as the cap rotates.

Whereas the cap assembly of the invention is particularly useful for closing the liquid opening of cell culture vessels, such as roller bottles and flasks, it is further anticipated that the inventive cap assembly would be useful for closure of an opening in a neck portion of a centrifuge tube or bottle, where it is important that the user not be required to apply a large amount of torque to attach and detach the cap. For example, following centrifugation, there may be discrete layers of separated components in the liquid medium which have less chance of intermixing in situations where the user applies a low amount of torque when detaching the cap and retrieving the separated components from the centrifuge tube or bottle.

What is claimed is:

1. A cap assembly for closing the opening in a neck portion of a container comprising:

a cap body having a top wall, an orifice formed in said top wall, and a depending annular skirt for screw attachment to said neck portion of said container;

a plug seal attached to said orifice of said cap body; and at least one projecting ring for reducing surface contact between said cap body and said plug seal, said at least one projecting ring being located on an undersurface of said top wall of said cap body for engagement with said plug seal, said plug seal and said cap body being relatively rotatably coupled for independent rotation of said cap body with respect to said plug seal upon attachment and removal of said cap assembly from said neck portion of said container.

2. The assembly of claim 1, wherein said plug seal is free to rotate about the longitudinal axis of said cap body.

3. The assembly of claim 1, wherein said orifice is stepped to assist in providing snap-fit attachment with said plug seal.

4. The assembly of claim 1, wherein said plug seal includes flanges which are integrally formed with a top surface of said plug seal to assist in providing a snap-fit attachment with said cap body.

5. The assembly of claim 4, wherein said flanges are configured in a discontinuous annular ring for association with said central orifice of said cap body.

6. The assembly of claim 1, wherein said plug seal further includes an annular groove.

7. The assembly of claim 6, wherein said top wall of said cap body further includes at least one depending projection spaced radially from said depending annular skirt of said cap body to be received in said annular groove of said plug seal.

8. The assembly of claim 7, wherein said projection is annular.

9. The assembly of claim 7, wherein said projection is discontinuous.

10. The assembly of claim 1, wherein said projecting ring is integrally formed with said cap body.

11. The assembly of claim 1, wherein said cap body includes two of said projecting rings.

12. The assembly of claim 1, wherein said annular skirt of said cap body includes an inner wall and an outer wall.

13. The assembly of claim 12, wherein said inner wall of said annular skirt includes threads for removably attaching the cap assembly from said neck portion of said container.

14. The assembly of claim 12, wherein said outer wall of said annular skirt is textured.

15. The assembly of claim 12, wherein said inner wall of said annular skirt includes a protruding locking arrangement positioned and formed to hold the cap assembly in a locked position on said neck portion of said container while maintaining the container in communication with an environment surrounding said container.

16. The assembly of claim 1, wherein said plug seal includes a bottom surface having tabs spaced in an annular arrangement for insertion of a gas-permeable membrane to form a vented cap assembly.

17. The assembly of claim 1, wherein said cap body is formed of a thermoplastic material.

18. The assembly of claim 1, wherein said plug seal is formed of a thermoplastic material.

19. The assembly of claim 1, wherein said plug seal extends into said orifice.

* * * * *